United States Patent [19]

Rubin

[11] 4,424,348

[45] Jan. 3, 1984

[54] METHODS OF MANUFACTURE OF NITRILE-CONTAINING GLUCURONIC ACID CONJUGATES

[75] Inventor: David Rubin, 5 Rav Zair, Jerusalem, Israel

[73] Assignees: Adolf W. Schwimmer, Savyon; Irwin Steven Schwartz, Tel Aviv; David Rubin, Jerusalem, all of Israel

[21] Appl. No.: 951,270

[22] Filed: Oct. 13, 1978

[51] Int. Cl.$^3$ .................. A61K 31/70; C07H 15/18
[52] U.S. Cl. ...................... 536/17.9; 536/4.1; 536/18.5; 536/55.3; 536/124; 424/180
[58] Field of Search ............... 260/345.7; 536/4, 17.9, 536/18.5; 424/180

[56] References Cited

FOREIGN PATENT DOCUMENTS 2212014 10/1972 Fed. Rep. of Germany .......... 536/4
122386 10/1976 German Democratic Rep. ..... 536/4

OTHER PUBLICATIONS

Trux, "New Controversy Surrounds Black Market Cancer Drug," *New Scientist*, Jul. 15, 1976, pp. 132–133.
Bicker, "Nature", 252, pp. 726–727, 1974.
Gullino, et al., "Jour. of the National Cancer Institute" 34, 6, pp. 857–869, 1965.
Lupo, et al., "Minerva Med." 67, (30), pp. 1973–1981, 1976.
Von Ardenne et al., "Agressologie", 17, 5, pp. 261–264, 1976.
Sweeney, et al., "Cancer Research", 31, pp. 477–478, 1971.
Baba, et al., "Gann", 69, pp. 283–284, 1978.
Ball, et al., "Biochem. Pharm." 23, pp. 3171–3177, 1974.
Levi, L. et al., "Laetrile: A Study of its Physical Chemical and Biochemical Properties", *Canad. Med. Ass. J.*, May 15, 1965, vol. 92, pp. 1057–1061.
Price, J. H. et al., "Laetrile–An Overview", *The Journal of School Health*, Sep. 1978, pp. 409–416.
*Federal Register*, vol. 42, #151, Friday, Aug. 5, 1977, pp. 39768+.
Progress Reports No. 28–33, Merck Sharp and Dohme Research Laboratories, "Quarterly Project Report to Cancer Chemotherapy National Service Center, Contact PH-43-62-479", Jan. 1965 through Jun. 1966.
"The Treatment of cancer with 'Laetriles': a report by the Cancer Commission of the California Medical Association", *California Medicine*, vol. 78, No. 4, pp. 320–326, Apr. 1953.
"The Magic Bullet that Missed", *Chemical and Engineering News*, vol. 31, 1540–1541, 1953.

*Primary Examiner*—Johnnie R. Brown
*Attorney, Agent, or Firm*—Browdy and Neimark

[57] ABSTRACT

Mandelonitrile-β-D-glucuronic acid is produced by condensing a mandelic amide with a tri-O-acetyl methyl ester of glucuronic acid and then reacting the product with acetic anhydride to produce the tri-O-acetyl methyl ester of mandelonitrile-β-D-glucuronic acid. The protecting acetyl groups may be removed and the barium salt formed by reacting with barium hydroxide, which salt, when treated with sulfuric acid, will yield the mandelonitrile-β-D-glucuronic acid. This compound, as well as methacrylonitrile β-D-glucuronic acid may be used in the treatment of bacterial infections having β-glucuronidase activity.

4 Claims, No Drawings

METHODS OF MANUFACTURE OF NITRILE-CONTAINING GLUCURONIC ACID CONJUGATES

CROSS-REFERENCE TO RELATED APPLICATION

The present application is related to a second application by the present applicant filed on even date herewith, Ser. No. 951,269, entitled "β-Glucuronidase Activity and/or pH-Dependent Pharmaceuticals and Their Methods of Production and Use for Selective Treatment of Diseases", the entire contents of which are hereby incorporated by reference.

FIELD OF THE INVENTION

The present invention relates to novel nitrile-containing glucuronides. The present invention also relates to processes for the synthesis of mandelonitrile-β-D-glucuronic acid.

BACKGROUND OF THE INVENTION

It has been suggested in British Pat. No. 788,855 that mandelonitrile-β-D-glucuronic acid may be used in the treatment of malignant tumors as β-glucuronidase is prevalent in malignant tissues and will selectively attack mandelonitrile-β-D-glucuronic acid at the site of the malignant tumors to split off hydrogen cyanide. U.S. Pat. No. 2,985,664 is also related to mandelonitrile-β-D-glucuronic acid and a method of producing same. These compounds have been named Laetrile by the patentees of the above mentioned patents.

It has been discovered, however, that none of the methods of producing this compound set forth in the above mentioned patents are reproducible. The present inventor has discovered that attempts to oxidize prunasin produce the glucuronide of mandelic acid because the CN group is unstable. Attempts to condense mandelonitrile with glucuronic acid or glucuronolactone or tetra-acetyl-glucuronolactone halogenide failed because the mandelonitrile tends to polymerize.

An article by Fenselau, C. et al in Science, volume 198, Nov. 11, 1977, pp. 625-7, entitled "Mandelonitrile β-Glucuronide: Synthesis and Characterization" confirms that the synthesis described in the original patents has not been reproduced. This article also confirms that while it was mandelonitrile-β-D-glucuronide which was originally given the name Laetrile, this compound does not appear in the Mexican preparations marketed as Laetrile. The major component of preparations currently marketed as Laetrile is amygdalin which may be easily prepared from natural source material, such as kernels of apricots, almonds, and other members of the Prunus family. However, amygdalin cannot be split by the enzyme β-glucuronidase.

The Fenselau reference teaches a method for the biosynthesis of mandelonitrile β-D-glucuronic acid. While this method may be satisfactory for producing laboratory amounts of the compound, such a biosynthetic process would no doubt be very difficult and costly to commercialize.

SUMMARY OF THE INVENTION

Accordingly, it is an object of the present invention to overcome the deficiencies of the prior art.

It is another object of the present invention to provide a new compound and pharmaceutical compositions which have very low toxicity to the human organism as a whole but very high selective toxicity toward bacterial cells having high β-glucuronidase activity.

It is yet another object of the present invention to provide processes for preparing the compounds of the present invention.

It is still another object of the present invention to provide a process for preparing mandelonitrile β-D-glucuronic acid by totally chemical synthesis.

These and other object of the present invention will be better understood from a reading of the following summary and the detailed description of the present invention.

In the above mentioned copending application referred to hereinabove, a process is disclosed for synthesizing glucuronides in which the aglycone is a strong electron acceptor. It is known that the glucuronide will become deconjugated (hydrolyzed) when attempting to convert the methyl ester to the acid in accordance with the classical processes. It is disclosed in this copending application that if barium hydroxide is used, the methyl ester of the aglycone of the glucuronide may be converted to the barium salt, and the barium salt may be converted to the free acid by the use of sulfuric acid without deconjugation of the glucuronide. Moreover, removal of the acetyl protecting groups is accomplished in the same step, thus eliminating the need of a separate step to accomplish this function.

This novel step using barium hydroxide is also used in the present method of synthesizing mandelonitrile β-D-glucuronic acid. However, the process of said copending application will fail when attempting to synthesize mandelonitrile β-D-glucuronic acid because when attempting to condense the methyl (tri-O-acetyl α-D-glucopyranosyl)halide-uronate with mandelonitrle, the mandelonitrile will tend to polymerize rather than to create the hemi-acetal bond with the glucuronic acid.

The method of synthesis in accordance with the present invention comprises first converting mandelic acid to mandelic amide by reaction with gaseous ammonia. The mandelic amide is then reacted with the methyl(tri-O-acetyl α-D-glucopyranosyl)bromide-uronate to produce the methyl ester of the mandelic amide triacetyl glucuronic acid. This compound may then be mixed with acetic anhydride to convert the mandelic amide to mandelonitrile. Treatment with barium hydroxide and sulfonic acid will produce the mandelonitrile β-D-glucuronic acid.

Both mandelonitrile β-D-glucuronic acid and methacrylonitrile β-D-glucuronic acid have antibacterial activity, particularly against those types of bacteria having β-glucuronidase activity. It is known, for example, that streptococci, staphylococci, and E. coli bacteria have β-glucuronidase activity. Therefore, if the glucuronides come into contact with these bacteria, they will become deconjugated and the cytotoxic aglycones will be toxic to the bacteria.

It has been reported that the optimum pH of bacterial β-glucuronidase is higher than the optimum pH of the β-glucuronidase of normal healthy internal organs, such as liver, spleen, kidney, etc. Therefore, upon alkalinization of the body in accordance with the method disclosed in said copending application, the β-D-glucuronidase activity of the organs will be substantially eliminated, while tht of the bacteria, although alkalinized, will still be present. The administered glucuronide will then only be deconjugated to its active form at the site of the infection. Since tumor cells are not being treated for this utility, no hyperacidification step is necessary.

DESCRIPTION OF THE PREFERRED EMBODIMENTS

EXAMPLE I

Synthesis of Mandelonitrile β-D-glucuronic Acid

Mandelonitrile β-D-glucuronic acid may be synthesized, in accordance with the present invention, from methyl(tri-O-acetyl-α-D-glucopyranosyl bromide)-uronate, which is the active form of glucuronic acid, and may be produced in accordance with the teachings of Bollenback, G. N., et al, *J. Am. Chem. Soc.* 77, 3310, (1955). Since this compound cannot be directly conjugated with mandelonitrile, mandelic amide is first formed. This compound is formed by bubbling gaseous NH3 into mandelic acid at 0° C. as illustrated in reaction:

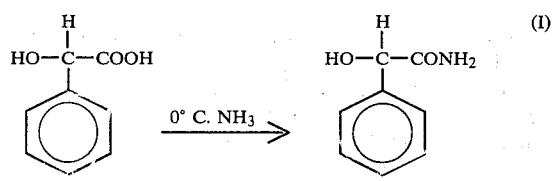

The mandelic amide is introduced to the methyl(tri-O-acetyl α-D-glucopyranosyl)bromide uronate in a solution of phenol catalyzed by a small catalytic amount of silver oxide. Besides phenol, there may be used, as solvent, quinoline, methyl nitrile or methyl cyanide. Silver carbonate may also be used as the catalyst. Another method of condensation is to use sodium or potassium hydroxide as the condensing agent in aqueous acetone solution. A stoichiometric excess of mandelic amide is preferably used. The reaction solution is maintained at room temperature for 24 hours or until the reaction is complete. The reaction is illustrated as follows:

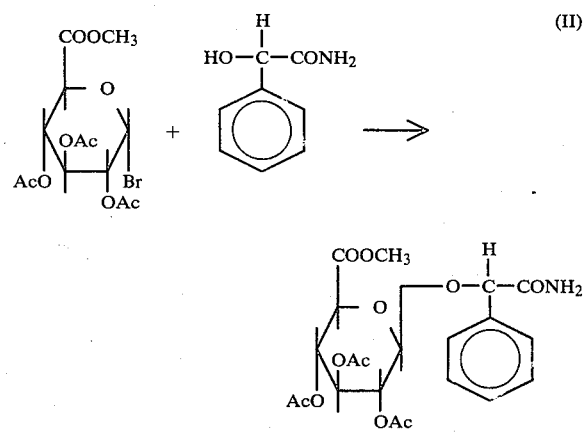

The above solution is then mixed with acetic anhydride in 1:1 molar ratio and heated to 70° C. for 30 minutes in order to convert the mandelic amide to the mandelonitrile in accordance with the following reaction:

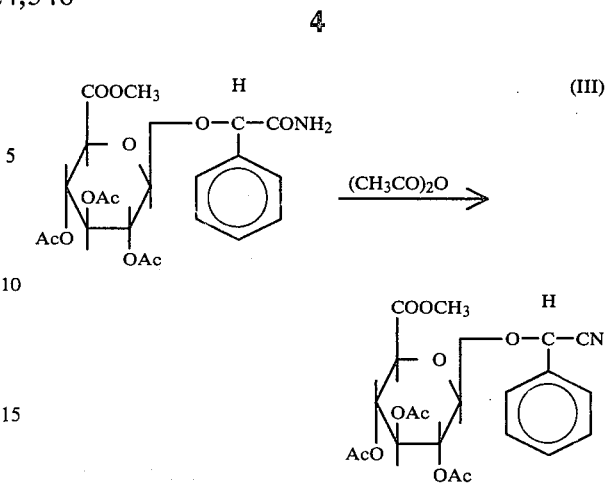

The acid is produced by reaction of the triacetyl methyl ester obtained by reaction (III) with a ½ molar amount of 0.5 N barium hydroxide which is added slowly to this solution to form a white precipitate. Preferably an excess of barium hydroxide is added until there is no more precipitation. The reaction can be illustrated as follows:

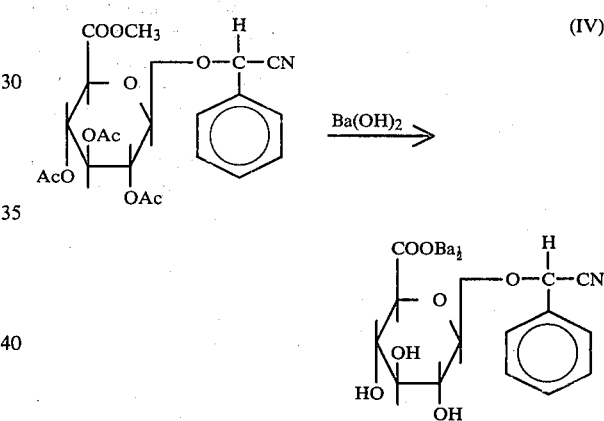

The addition of 0.5 N sulfuric acid, volume to volume, then cooling in ice water for 20 minutes, releases the free glucuronides according to the following reaction:

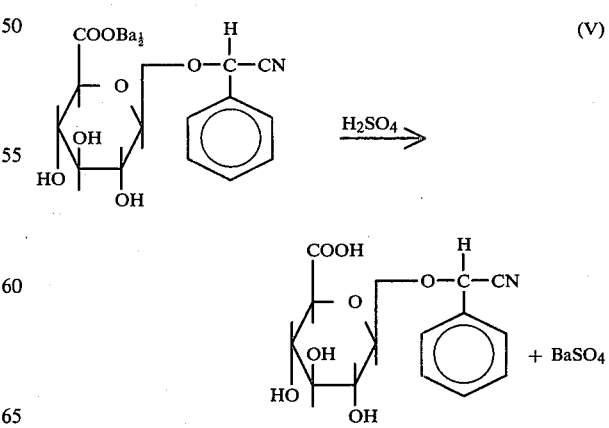

The mixture is then filtered and the supernatant is dried in vacuum and crystallized from ether.

The free acid form of the glucuronide, or a salt thereof which will ionize at the conditions of use, is the preferred form of the compounds to be used in accordance with the present invention. However, pharmaceutically acceptable esters may also be used, although in most cases it would be expected that their activity would be somewhat less due to their relatively lower affinity to β-glucuronidase. This is particularly true with respect to aglycones which are strong electron acceptors. Accordingly, whenever the term "glucuronide compound" is used in the present specification and claims it is understood to include not only the free glucuronic acid form of the conjugate but also pharmaceutically acceptable salts and esters thereof as discussed hereinabove.

EXAMPLE II

Synthesis of Methacrylonitrile β-D-Glucuronic Acid

Methacrylonitrile β-D-glucuronic acid or other glucuronides of nitrile-containing cytotoxic compounds may be produced in accordance with the present invention in a manner similar to that disclosed in Example I, although the step of converting the methacrylonitrile to methacrylamide prior to condensation with methyl(tri-O-acetyl-α-D-glucopyranosyl bromide)-uronate will not be necessary as there is not the same polymerization problem with methacrylonitrile as there is with mandelonitrile. In general, the preferred process when condensing the aglycone directly, is to react the stoichiometric excess of the aglycone (methacrylonitrile in the case of methacrylonitrile β-D-glucuronic acid) with the methyl(tri-O-acetyl-α-D-glucopyranosyl bromide)-uronate in 5 N potassium hydroxide and maintaining the reaction solution at room temperature for 24 hours. The solution is then diluted with 3 volumes chloroform and the chloroform-acetone layer washed with water and dried. After removal of the solvent, the crystals which are obtained are treated with a one half molar amount of barium hydroxide to produce the barium salt which is then treated with an equimolar solution of sulfuric acid to produce the free glucuronide.

EXAMPLE III

Acute Intravenous Toxicity To Rabbits of Mandelonitrile β-D-Glucuronic Acid

NZW rabbits in the weight range of 2,000 to 3,200 g for females and 2,200 to 3,800 g for males were injected intravenously with mandelonitrile β-D-glucuronic acid solution. Rabbits injected with saline alone served as the control. The mandelonitrile β-D-glucuronic acid solution contained 10% mandelonitrile.

During the 14 day observation period a record was kept of all mortalities and signs of toxicity. Table I gives the range finding screen.

TABLE I

Mortality Data for Groups of Rabbits (2 per Group) Intravenously injected with DMBG Solution. Range Finding Screen

| Dosage ml/kg | Mortality Ratio no. of deaths/ no. dosed |
|---|---|
| 0.25 | 0/2 |
| 0.5 | 1/2 |
| 1.0 | 2/2 |
| 2.0 | 2/2 |
| 4.0 | 2/2 |

The results of the preliminary range finding tests as shown in Table I indicated that the median lethal intravenous dose (LD-50) was in the region of 0.23-2 ml per kg body weight.

Dosing was then extended to larger groups of rabbits (5 males and 5 females per group) in order to locate the median lethal dose more precisely. Table II gives mortality data for this larger group.

TABLE II

Mortality Ratio of Rabbits Intravenously Injected with DMBG Solution. Full Scale Test - Weight range: Females 2,000-3,200 g, Males 2,200-3,800 g.

| | Dosage ml/kg | Mortality ratio no. of deaths/ no. dosed | Time of death after dosing no. of animals | no. of hours |
|---|---|---|---|---|
| 15 Males | 0.44 | 0/5 | — | — |
| | 0.66 | 2/5 | 2 | <3 |
| | 1.0 | 3/5 | 3 | <3 |
| | 1.5 | 4/5 | 4 | <3 |
| | 2.25 | 5/5 | 5 | <3 |
| 20 Females | 0.44 | 0/5 | — | — |
| | 0.66 | 2/5 | 2 | <3 |
| | 1.0 | 5/5 | 5 | <3 |
| | 1.5 | 5/5 | 5 | <3 |
| | 2.25 | 5/5 | 5 | <3 |

Signs of reaction to treatment, observed 2 minutes after dosing, included ataxia and paralysis. Two minutes later a few animals of the high dose group died. All the deaths of all the groups occurred within 3 hours after dosing. The animals which survived did not show any clinical symptoms during the following 14 days. Autopsy of all animals did not show clear gross pathological changes.

The acute median lethal intravenous dose (LD 50) and its 95% confidence limits calculated by the method of Weil, C. S., 1952, Biometrics, 8:249, to rabbits of mandelonitrile β-D-glucuronic acid 10% solution are calculated to be: males 0.84187 (0.78087-0.90287) ml/kg body weight females 0.6873 (0.64417-0.73043) ml/kg body weight.

From the above data, it is believed that the maximum safe dose is on the order of 0.44 ml/kg body weight, and it is believed that this limit should not be exceeded in human therapy.

EXAMPLE IV

Method of Administration

After it has been determined that the patient has a bacterial infection with β-glucuronidase activity, the first step of the treatment is to begin an intravenous drip of a solution in distilled water containing approximately 60 milliequivalents sodium bicarbonate. Approximately 1 liter is administered, assuming no contraindications, and the pH of the urine is checked to determine that it has reached a pH of approximately 7.4. This will establish that the system has become alkalinized and it is now safe to administer the glucuronide. Another liter of the same bicarbonate solution, but also including the desired amount of mandelonitrile β-D-glucuronic acid is then administered. Either immediately before, during or after administration of the mandelonitrile β-D-glucuronic acid 50 cc of a 25% solution of sodium thiosulfate is administered, preferably intravenously by slow drip. The sodium thiosulfate is preferably included in the bicarbonate-glucuronide solution which is being dripped intravenously. However, it may also be continued afterward for a greater margin of safety. This entire procedure may be repeated daily as needed.

If there are contraindications for the administration of bicarbonate, then antacid may be orally administered. The important criterion is that the pH of the urine become approximately 7.4 and remain so during treatment.

Any agent which will raise the pH of the urine to approximately 7.4 can be used as the alkalinizing agent, including sodium or potassium bicarbonate or citrate or other basic salts or antacids. While it is preferred that these be administered intravenously, they may be administered orally.

When the term "approximately 7.4" is used in the present specification and claims, with respect to the pH level to be maintained in the rest of the body, it should be understood that a pH level slightly above or below 7.4 may be used, although not preferred. As the pH decreases from 7.4 the $\beta$-glucuronidase activity increases (until the optimal pH is reached). Furthermore, below pH 7.0 the rest of the body will not be alkaline but will be acid. Above 7.4 the danger of alkalosis increases without any substantial further decrease in $\beta$-glucuronidase activity. A pH level of 7.4 is preferred as this is physiological pH and cannot be harmful to the body and it is known that the $\beta$-glucuronidase activity in healthy organs is substantially nil at this pH level.

The dosage of the glucuronides should be monitored to avoid any side effect. It may be preferable to treat with glucuronides in short courses of several days, leaving several days in between before the further treatment continues.

Besides intravenous administration, the mandelonitrile $\beta$-D-glucuronic acid may be administered by any means of parenteral administration. Glucuronides should not be administered orally as it is known that $\beta$-glucuronidase is present in the digestive tract. The sodium thiosulfate, however, can be administered orally if a proper enteric coating is provided to avoid release in the stomach.

While the present Example is directed specifically to the administration of mandelonitrile $\beta$-D-glucuronic acid, it should be understood that glucuronides of other nitrile-containing cytotoxic aglycones, such as methacrylonitrile $\beta$-D-glucuronic acid will be administered in the same manner. The amount of glucuronide to be administered to any given patient must be determined empirically and will differ on the condition of the patient. Relatively small amounts of glucuronide can be administered at first with steadily increasing daily dosages if no adverse effects are noted. Of course, the maximum safe toxicity dosage as determined in routine animal toxicity tests should never be exceeded.

EXAMPLE V

Biosynthesis of Mandelonitrile $\beta$-D-Glucuronic Acid

A 22 cc solution of 5% mandelonitrile (banzaldehyde cyanohydrin) in propylene-glycol is prepared and an intramuscular injection of this solution is given to a donkey or a goat. The 24 hr. urine is collected and acidified with acetic acid until the pH becomes 4. The urine is then filtered through a fiberglass filter and the filtrate is treated in any one of the following three different ways:

A. A saturated solution of lead acetate is added to the filtrate. The white precipitate that appears is separated by centrifuge and filtered. The filtrate is alkalined with NH3 to pH 8 and then a saturated solution of basic lead acetate is added. The precipitate is washed with cold water and gaseous H2S is bubbled into it, the black precipitate of lead sulfide being separated. The filtrate is put into a vacuum until the volume is reduced to one third. A brown paste is achieved which is dissolved in absolute alcohol and kept overnight. The solution is filtered and the filtrate is vacuumized and ether added. The mandelonitrile $\beta$-D-glucuronic acid is crystallized from the ether solution.

B. The urine is acidified with hydrochloric acid to pH 4 and filtered through a fiberglass filter. Afterwards, the solution is dried in a vacuum state and the residue is dissolved in ether and recrystallized from the ether solution.

C. 0.1 N barium hydroxide water solution is added to the urine. The white precipitate of the barium salt of the mandelonitrile glucuronide is then washed in cold water and stirred and 0.1 N sulfuric acid is added. An insoluble solution of barium sulfate is removed and the supernatant vacuum dried and then recrystallized from ether solution.

Since mandelonitrile is very toxic and only a very small amount can be administered, the following semi-biosynthetic procedure may be used.

20 g mandelic amide (2-hydroxybenzamide) is mixed with goat or donkey food and the urine is collected for 24 hours. The mandelic amide glucuronide is separated by any of the methods described hereinabove. Acetic anhydride is then added and the glucuronide (2,3,4-triacetate glucopyranose mandelonitrile) is precipitated with barium hydroxide. The barium is removed with sulfuric acid and the glucuronide is recovered in vacuum as described hereinabove.

It will be obvious to those skilled in the art that various changes may be made without departing from the scope of the invention and the invention is not to be considered limited to what is described in the specification.

What is claimed is:

1. A method for the production of mandelonitrile-$\beta$ D-glucuronic acid, comprising:
   condensing mandelic amide with methyl (tri-O-acetyl-$\alpha$-D-glucopyranosyl)halide-uronate to form the methyl ester of mandelic amide-tri-O-acetyl-$\beta$-D-glucuronic acid;
   reacting the product of said condensing step with acetic anhydride at a sufficient temperature and time to produce the methyl ester of mandelonitrile-tri-O-acetyl-$\beta$-D-glucuronic acid;
   adding to the product of said reacting step a sufficient quantity of barium hydroxide to produce a white precipitate;
   separating said precipitate;
   treating said precipitate with a sufficient quantity of sulfuric acid until precipitation of barium sulfate is completed;
   removing the supernatant from the product of said treating step; and
   drying said supernatant to obtain mandelonitrile-$\beta$-D-glucuronic acid.

2. Methacrylonitrile-$\beta$-D-glucuronic acid.

3. A method in accordance with claim 1 wherein said condensing step is accomplished in solution in quinoline, phenol, methyl nitrile or methyl cyanide catalyzed by silver oxide or siver carbonate.

4. A method in accordance with claim 1 wherein said condensing step is accomplished in aqueous acetone solution in the presence of sodium or potassium hydroxide.

* * * * *